United States Patent [19]

Lennox et al.

[11] Patent Number: 4,760,026
[45] Date of Patent: Jul. 26, 1988

[54] MONOCLONAL ANTIBODY

[75] Inventors: Edwin S. Lennox, Great Wilbraham; Steven H. Sacks, Cambridge, both of United Kingdom

[73] Assignee: Celltech Limited, Berkshire, England

[21] Appl. No.: 931,880

[22] Filed: Nov. 17, 1986

Related U.S. Application Data

[63] Continuation of Ser. No. 438,896, filed as PCT GB/00076 on Mar. 8, 1982, published as WO82/03089 on Sep. 16, 1982, abandoned.

[30] Foreign Application Priority Data

Mar. 6, 1981 [GB] United Kingdom ................. 8107179

[51] Int. Cl.$^4$ ................. A61K 39/395; G01N 33/577; C12N 15/00
[52] U.S. Cl. ....................................... 530/387; 435/7; 435/172.2; 435/948; 435/240.27; 424/11; 530/808; 530/809; 935/103; 935/110
[58] Field of Search ................... 435/68, 41, 240, 241, 435/948, 7, 172.1, 172.2, 948; 530/387, 808, 809; 424/11; 935/103, 110

[56] References Cited

U.S. PATENT DOCUMENTS 2,454,752  11/1948  Coca ..................................... 424/11
4,297,274  10/1981  Bohn et al. ...................... 260/112 B
4,350,683   9/1982  Galfre .................................... 435/7

OTHER PUBLICATIONS

Lloyd et al., (1968), Biochemistry, vol. 61, pp. 1470–1477.
Chemical Abstracts, vol. 89, 1978, item #40562d, Journal of Supramolecular Structure, 1978, 8(1), 78–88.
Chemical Abstracts, vol. 94, 1981, item #2831m, Journal of Clinical Pathology, 1980, 33(10), 958–62.
Kohler et al., (1976), European Journal of Immunology, vol. 6, pp. 511–519.
Eisen, (1974), Immunology, Harper and Row Publishers, Hagerstown, Md., pp. 600–604.
Joysey, U. C., Brit. Med. Bull., vol. 15, No. 2, pp. 158–164, (1959).
Rechtsmedizin, vol. 89, pp. 101–104, (1982).
Sacks et al., "Monoclonal Anti-B as a New Blood-Typing Reagent", Vox Sanguinis, vol. 40, No. 2, (Feb. 1981), pp. 99–104.
Voak et al., "Monoclonal Anti-A from a Hybrid-Myeloma: Evaluation as a Blood Grouping Reagent", Vox Sanguinis, vol. 39, No. 3, (Sep. 1980), pp. 134–140.
Feizi et al., Journal of Experimental Medicine, vol. 149, (Apr. 1979), pp. 975–980.
Childs et al., European Journal of Immunology, vol. 10, (1980), pp. 379–384.
Nature, vol. 266, pp. 550–552, (1977).
Milstein et al., 1CN UCLS Sumposia on Molecular and Cellular Biology, (1977).
Nature, vol. 256, p. 495.
Eur J. Immunology, 1976, pp. 511–519.
Nature, vol. 266, p. 495.
Medical Laboratory Sciences, vol. 36, (1979), p. 335.
British Search Report
Leincet 11-6-77, p. 1242.
Antibodies in Human Diagnosis and Therapy, pp. 271–284.
Chem & Eng, News 1-1-79, pp. 15–17.

Primary Examiner—Esther M. Kepplinger
Assistant Examiner—William J. Herald
Attorney, Agent, or Firm—Cushman, Darby & Cushman

[57] ABSTRACT

A monoclonal antibody having specificity for an antigenic determinant of a B-type blood cell. The monoclonal anti-B, produced by a hybridoma cell (the preparation of which is described), affords a defined, specific and cheap blood grouping reagent. The monoclonal antibody is defined by its specificity and functional affinity.

6 Claims, 4 Drawing Sheets

MONOCLONAL ANTIBODY

This is a continuation of application Ser. No. 438,896, filed as PCT GB/00076 on Mar. 8, 1982, published as WO82/03089 on Sep. 16, 1982, now abandoned.

FIELD OF THE INVENTION

This invention relates to the field of biotechnology and concerns particularly the use of a monoclonal antibody as a blood grouping reagent.

BACKGROUND OF THE INVENTION

The introduction of foreign material (antigenic material) into the body of a vertebrate animal provokes an immune reaction, the intent of which is to prevent the antigenic material causing damage to the body and to facilitate the removal of such material from the body. The immune system achieves this by producing immunoglobulin molecules (hereafter referred to as antibodies) which have the property of selectively recognising and binding to characteristic sites on the antigenic material. These sites are known as determinants and an antigen may possess one or more such determinants. Antibodies generated by the immune system each have specificity to only one determinant but a number of different antibodies may be produced if the antigenic material against which antibodies are raised possesses more than one determinant.

The primary function of antibodies is to protect the body from harmful foreign material, by agglutinating it, thereby assisting the normal body processes to remove the material.

The agglutination of antigenic material by antibodies does however have a practical use outside the body in the field of blood grouping.

Red blood cells (erythrocytes) have on their surface a number of different, and distinctive antigenic determinants, the character of which determinants allows the classification of blood into groups, or types (for example, A, B, O, $A_1B$, $A_2B$, $B_{cord}$). It is essential in the transfusion of blood from a donor to a recipient that the transfused blood be of the same group as that of the recipient's blood, for if it is not, the immune system of the recipient will generate antibodies against the unfamiliar determinants upon the surface of the transfused erythrocytes. The reaction of such antibodies with foreign erythrocytes forms the basis of the technique of blood grouping.

In broad terms the grouping of blood samples relies upon the detection of agglutination or otherwise of erythrocytes in the sample when antiserum to the determinants found on the surface of that group of erythrocytes is added. The agglutination is a macroscopic effect which can be readily discerned by eye or detected automatically by machine.

The major source of blood grouping reagents has hitherto been through the hyperimmunisation of human subjects. This involves the introduction into a human subject of a substantial, but non-lethal, dose of a blood serum of a type different from that of a human subject. This provokes the normal immunological response resulting in the production of antibodies in the blood of the subject, a sample of which blood may be subsequently removed and an antibody preparation made therefrom. Such a preparation may be used to group an unknown blood sample since it will cause a visible flocculation or agglutination of the erythrocytes if the unknown blood sample is of the same type as originally introduced into the human serum donor.

In practice there are two types of blood grouping test. (Dunsford, F.; Bowley, C.: Techniques in blood grouping: 2nd Ed (1967). In the first, a sample of blood to be grouped is placed upon a blood grouping tile (see: British Pharmacopeoia: Determination of ABO donors). This is then mixed upon the tile with a sample of antiserum. Any subsequent agglutination indicates that the unknown sample of blood being grouped belongs to the same blood group as the group against which the antiserum was raised. In practice such tile agglutination grouping tests are routinely carried out in emergencies.

In the second type of experiment the blood sample to be grouped is placed together with an antiserum in saline solution in a tube and allowed to stand for a standard period (2 hours). The presence of agglutination may then be estimated by the sedimentation that has occurred within the standard period. Under emergency conditions a centrifuge may be used to expedite the test.

The efficacy of a particular blood grouping reagent is judged by the speed with which it forms agglutinants and by the manner in which its ability as an agglutinin varies with concentration.

The former of these criteria is commonly referred to in the art as "avidity". The avidity time of a particular blood grouping reagent is defined as the time taken for the mixing of the blood sample with the reagent to the time at which a noticeable agglutination of the sample has occurred.

In order to determine the dilution characteristics of a blood grouping reagent a saline agglutination titre may be measured. This measurement comprises preparing a number of equal volume, 2 fold, series, saline dilutions of the blood grouping reagent to be tested. To each dilution sample is added a known amount of the appropriate erythocyte suspension. The same amount of suspension is added to all dilutions. Each dilution sample is left to stand for a standard period (usually 2 hours) at the end of which an agglutination count is made under a microscope. The sample of highest dilution at which substantial agglutination occurs is determined and that dilution is termed the "saline agglutination titre". A reagent having a high saline agglutination titre is therefore a potent agglutinin.

Two problems are evident with the production of antibodies to erythrocyte determinants using the technique of hyperimmunisation of a human subject. Firstly, donations of blood serum are in limited supply and nowadays with the increasing frequency of major surgery the need for blood grouping has increased markedly. This places a strain on the supply of human blood serum which is also in damand for other medical uses. In addition, the agglutination effect of naturally produced antibodies to erythrocytes tends to give somewhat variable results. One reason for this effect is that the immune response prepares a 'cocktail' of antibodies each component of which cocktail has a specific action on a determinant as discussed above. It is impossible to separate the various antibodies in this cocktail and so conventional antisera contain mixtures of antibodies and the mixtures vary from animal to animal (even within the same genus and from day to day). The same set of determinants is not present on all erythrocytes of the same group, which results in the response being in many cases very variable.

In summary a reagent suitable for blood grouping must be:

(1) specific for the appropriate antigen, (2) sufficiently potent to give good macroscopic reactions to the weaker blood groups by emergency as well as routine methods of blood grouping, (3) stable under the conditions of use, and (4) readily available at reasonable cost.

Recent advances in molecular biology have provided a technique for the production of highly specific antibodies by the production of a hybrid cell (or hybridoma) from an antibody-producing spleen cell and a myeloma cell. This technique, the work of Kohler and Milstein (Eur. J. Immunol. 6, 292–295 (1976); Nature 256, 495–497 (1975); Eur. J. Immunol. 6, 511–519 (1976) provides a method for producing a limitless source of antibody. The antibodies produced are termed monoclonal antibodies since the hybrid cell elaborating them produces only one type of immunoglobulin molecule i.e. only immunoglobulin specific to one determinant. Hybridoma cells combine the two desirable features of myeloma cells and lymphocytes. That is myeloma cells have an immortal character and can self-replicate in vitro, whilst lymphocytes have the desirable property of expressing antibodies. Such hybrid cells are therefore a permanent source of pure, defined immunoglobulin. The process used for producing hybrid cells commonly comprises the steps of immunising a mouse with the appropriate antigen and after allowing sufficient time for the immune reaction to take place, sacrificing the animal and removing its spleen. A cell suspension may then be prepared from the spleen, and this suspension is mixed with a suspension of mice myeloma cells. Polyethylene glycol may be used to promote fusion of the two cells. The resulting individual hybridoma cultures, having derived from one lymphocyte cell, specifically produce one type of antibody, that is an antibody specific to one particular determinant.

This technique has been used by Voak et al (Vox Sanguinis 39 134–140 (1980)) to produce a monoclonal antibody to the determinants of A-type erythrocytes and such monoclonal anti-A's have been shown to be useful blood grouping reagents.

However, it has widely been thought that the immunisation of mice wth B-type human blood cells will not produce spleen cells capable of fusion with myeloma cells to form hybridoma cells elaborating anti-B immunoglobulin.

We have surprisingly found that this is not the case and that successful fusions may be readily obtained, resulting in hybridoma cells expressing monoclonal anti-B with high efficiency thereby producing a high avidity specific blood grouping reagent with a useful saline agglutination titre profile. Furthermore, it has proven possible to define an equilibrium constant and a dissociation rate constant for the immunocomplex formed between the monoclonal anti-B and B type blood cells. Hitherto such quantitative analysis of the strength of the immunocomplex formed between a blood grouping reagent and red blood cells has not been possible since previously known blood grouping reagents have comprised mixtures of immunoglobulin of differing specificity. The best figure that could be achieved formerly was therefore an average value.

STATEMENT OF INVENTION

According to the present invention we provide a monoclonal antibody which has specificity for an antigenic determinant of a B-type blood cell.

In this context the term B-type blood cell is to be taken to include all red blood cells possessing one or more antigenic determinants found solely upon B-type blood cells. Examples of blood types which have such determinants are B, $A_1B$, $A_2B$ and $B_{cord}$.

The monoclonal antibody is preferably a mouse, IgM, monoclonal anti-B immunoglobulin.

Preferably the monoclonal antibody is capable of causing agglutination of a sample of B-type blood having the said determinant. We have found that particularly useful such properties result when the monoclonal antibody is such that the equilibrium constant of the interaction between said antibody and B-type blood cells is greater than $1.3 \times 10^7 M^{-1}$, especially when such equilibrium constant is greater than $1.2 \times 10^8 M^{-1}$. The values of the equilibrium constant referred to in this specification are functional affinities, that is to say measurements made of the interaction between polyvalent antibody (IgM) and red blood cells. In this respect they differ from intrinsic affinities which are derived for interactions between univalent antibody (IgG) and antigen. Intrinsic affinities are not directly comparable to functional affinities. Values calculable for the monoclonal antibody of the present invention are subject to the assay used, these being fully described in the description which follows of the characterisation of the monoclonal antibody.

According to another aspect of the invention, the monoclonal antibody is such that the rate constant of the dissociation reaction of an immunocomplex comprising said antibody and B-type blood cell of blood group B is less than $2.2 \times 10^{-2} sec^{-1}$ and preferably less than $7.6 \times 10^{-4} sec^{-1}$.

In another aspect of the invention the monoclonal antibody is such that the rate constant of the dissociation reaction of an immunocomplex comprising the monoclonal antibody and B-type blood cells of blood group $A_1B$ is less than $5.0 \times 10^{-2} sec^{-1}$ and preferably less than $3.4 \times 10^{-3} sec^{-1}$.

The values of the dissociation constant referred to in this specification are functional affinities as described above.

The invention also provides a process for preparing the said monoclonal antibody comprising injecting a mouse with a group B substance, sacrificing the mouse, removing its spleen and forming a suspension of spleen cells; fusing the spleen cells with mouse myeloma cells to form hybrid cells; cloning said hybrid cells; and causing said cloned hybrid cells to secrete said antibody.

Preferably the said hybrid cells, before cloning, are subjected to selection.

Preferably the said myeloma cells are NS1 cells. The invention also includes a monoclonal antibody produced by the process described above, hybridoma cells capable of secreting the said monoclonal antibody and a blood grouping reagent comprising the said monoclonal antibody.

GENERAL DESCRIPTION OF THE PREPARATION OF THE HYBRIDOMA CELLS

Suitable mice were found by assay of serum samples for anti-B activity after absorption with group O cells to remove anti-species antibodies. A mouse with an anti-B agglutination titre of 1:8 after absorption was injected intraperitoneally with 100 μg group B substance in 0.1 ml complete Freund's adjuvant (Difco Bacto), this was repeated 5 weeks later and boosted after a further 9 weeks with 200 μg B substance in 0.1 ml saline intravenously. Three days later the spleen was removed and a cell suspension was prepared.

Spleen cells ($10^8$) were fused with mouse myeloma NS1 cells ($10^7$) using polyethylene glycol (Cotton et al Eur. J. Immunol., 3, 135-140 (1973); Dunsford and Bowley see above; Galfre et al Nature, 266, 550-552 (1977)). Growing cell hybrids were selected by their ability to produce specific anti-B activity, detected in the culture supernatant by agglutination assays using human A, B and O erythroctes. Anti-B secreting hybrids were cloned twice on soft agar, grown up eventually into 1 liter spinner-cultures in Dulbecco's Modified Eagle's Medium (DMEM Gibco Biocult) supplemented with 5% v/v foetal calf serum (FCS, Sera-Lab). The cloned hybrids are stored in liquid nitrogen.

Tissue culture supernatant containing the monoclonal antibody was prepared by centrifugation to remove cells and debris, filtration through millipore filters and addition of 10 mM Hepes buffer and 0.1% sodium azide. Aliquots of each batch were then stored at 4° C. for routine use or −20° C. for stocks.

DETAILED DESCRIPTION OF THE MATERIALS AND METHOD USED IN THE PREPARATION OF THE HYBRID CELLS

Mice and Rats

B10.BR, C3H/He-mg and other mice were obtained initially from OLAC, 1976 Ltd (Bicester, GB) and then from Medical Research Council stocks bred from OLAC animals. AKR mice came from Banting and Kingman (York, G. B.). (C3H×BALB/c)F$_1$ mice and Lou, DA and AO rats were bred in the Medical Research Council animal house; Wistar, PVG, WAG and Sprague-Dawley rats were from Banting and Kingman.

Mice for testing and immunization were 6–8 weeks old.

Immunizations

Human Group B substance used in immunizations

Dr. W. Watkins (Clinical Research Centre, Harrow, G. B.) provided human B (and A) substance which is the phenol (95%) insoluble, ammonium sulphate (100%) insoluble, ethanol (45–55%) insoluble and watersoluble extract of freeze dried ovarian cyst fluid, derived by the method of Morgan (1965). They are glycoproteins, consisting of 80–85% carbohydrate (L-glucose, D-galactose, N-acetyl-D-flucosamine, N-acetyl-D-galactose), 15–20% amino acids (with a predominance of L-threonine, L-serine and L-proline) and 1–2% sialic acid. They were received lyophilized and were dissolved to 2 mg/ml in 0.9% saline and stored at −20° C.

PREPARATION OF AN EMULSION OF B SUBSTANCE IN COMPLETE FREUND'S ADJUVANT (CFA)

1 ml B substance at 2 mg/ml in 0.9% saline was added to 1 ml CFA (Difco Bacto, a mixture of Bayol F, oil and mannide oleate detergent and containing *Mycobacterium tuberculosis*). The mixture was vigorously homogenized in two 5 ml glass syringes (Chance, Warley, G. B.) connected at right angles by a 2-way tap and cooled intermittently on ice, until a white cream formed (takes 10–20 min) which did not disperse when a drop was placed on water. CFA is still one of the best potentiators of immune response (see Bomford, 1980). Repeat injections were given at different sites since granulomata may form.

Immunization Schedule

To find suitable mice, non-immunized animals were tail bled and the serum, after absorption with group O erythrocytes to remove anti-species antibodies, was assayed by tube agglutination with B erythrocytes.

Female B10.BR mice and C3H/He-mg mice aged 6–8 weeks having high anti-B titres were injected intraperitoneally (i.p.) with one of 3 preparations: 100 μg B substance in 0.1 ml CFA (see below), 10 μg B substance in the same or 0.1 ml packed group B erythroctes washed 4 times. Mice were tail bled 2 weeks later.

B10.BR mice which had high serum titres were given a repeat i.p. injection of 100 μg or 10 μg B substance at 5 weeks, or a repeat of 0.1 ml cells at 3, 4 and 5 weeks after the first injection. Mice were tail bled at 1 week, 3 weeks and 6 weeks after the last injection.

9 weeks after the 2nd injection of 100 μg, B10.BR mouse 2 was injected with 200 μg B substance in 0.1 ml saline. 3 days later the spleen was removed and a cell suspension was prepared for fusion with myeloma cells.

Collection of sera 0.5 ml tail blood collected in plastic tubes was allowed to clot at 37° C. for 1 h and loosened from the tube to aid clot retraction. Separated sera were diluted with 0.9% saline, incubated for 20 min in a 56° C. water bath and absorbed with O or A$_1$ cells as required. Aliquots were stored at −20° C.

Preparation of monoclonal antibodies to blood group B

The general outline of the procedures follows the basic principles laid down by Kohler and Milstein (see above for references) for making monoclonal antibodies with desired reactivity:

| | |
|---|---|
| Spleen cells | HGPRT ase +ve |
| | Specific Ig +ve |
| | Terminally differentiated |
| Myeloma cells | HGPRT ase −ve |
| | Specific Ig −ve |
| | Immortal |
| Hybrid cells | HGPRT ase +ve |
| | Specific Ig +ve |
| | Immortal |

Unfused myeloma cells lack HGPRT ase and hence die in selective medium (Littlefield, Science 145, 709–710 1964). Unfused spleen cells do not survive in tissue culture. Only hybrids of spleen cells and myeloma cells have both HGPRT ase and immortality and hence survive; those secreting antibody of the required specificity can then be selected, i.e. hybrid cells have the advantages of both parent cells.

Stock solutions

50% polyethylene glycol (P.E.G.) solution 10 g P.E.G. 1500 (BDH Lot 6573370) was autoclaved and transferred immediately to a 45° C. water bath, followed by addition of 10 ml DMEN at 37° C.

Aminopterin stock 1000X

Aminopterin (Sigma) was dissolved at 0.176 mg/ml in 0.008M NaOH slightly warmed, and stored in the dark at −20° C.

HT stock 100X 136.1 mg hypoxanthine (Sigma) and 38.75 mg thymidine were dissolved by boiling in 100 ml DDW and stored in 50 ml aliquots at −20° C.

50 ml DMEN 50 ml HT 100X

The made up solution was filtered (Millipore, pore size 0.22 μm) and stored in 13 ml aliquots at −20° C. On thawing, HT was redissolved by warming to 60°–70° C.

HAT medium 50X 45 ml DMEN 50 ml HT 100X 5 ml Aminopterin 1000X

The solution was filtered, stored and thawed as above in 13 ml aliquots.

HAT in 20% FCS-DMEN (HAT medium)1X 400 ml DMEN 100 ml FCS (Batch 901112)

8 ml P/S 8 ml Glutamine 6 ml Pyr.

10.6 ml HAT medium 50X ($1.0 \times 10^{-4}$M hyposanthine, $4.0 \times 10^{-7}$M aminopterin, $1.6 \times 10^{-5}$M thymidine)

HT in 20% FCS-DMM (HT medium)1X 10.6 ml HT 50X replaced HAT 50X in the above recipe. Thus, the following terms will be used:

| Serum free DMEM | = DMEM + PS + glut. + pyr. |
|---|---|
| 20% FCS—DMEM | = Serum free DMEM + 20% FCS |
| HAT medium | = 20% FCS—DMEM + HAT |
| HT medium | = 20% FCS—DMEM + HT |

Production and early selection of anti-B myeloma hybrids

Cell fusion was performed as described by Kohler et al., (see above for references). In preparation, the following media were equilibrated overnight at 37° C. in an atmosphere of 5% $CO_2$ in air (Leec incubator): 1) 50% PEG solution 2) serum-free DMEN and 3) 20% FCS-DMEN including 1.5 ml aliquots distributed in 48 Linbro wells.

On the morning of the fusion the spleen was removed aseptically and the cells were teased into 10 ml serum-free DMEN and transferred to a 10 ml centrifuge tube. Allowing 5–10 min for cell clumps to sediment, suspension cells were removed with a pipette and washed twice in serum-free DMEN. The one spleen gave $1.4 \times 10^8$ suspension cells. $10^8$ of these were collected in 5–10 ml serum-free DMEN. At the same time $10^7$ myeloma NSI cells growing in spinner culture at $2.6 \times 10^6$/ml were washed twice and resuspended in 5 ml serum-free DMEN.

Media containing spleen cells ($10^8$) and myeloma cells ($10^7$) were pooled in a 50 ml Corning tube and the cells were pelleted by centrifugation at 400 g for 5 min, RT. and the medium was aspirated as completely as possible using a Pasteur pipette attached to an aspirator pump. With the tube supported in a 37° C. beaker of water, 1 ml of 50% PEG solution (equilibrated, at 37° C.) was added gradually over 1 min, followed by gentle stirring for a further 1 min with the pipette tip used for addition. The suspension was then diluted by the slow addition of serum-free DMEN (equilibrated, at 37° C.) at 1 ml/min for 2 min, 2 ml/min for 4 min, 10 ml dropwise and then freely to 50 ml, gently agitating the tube with each addition. Following centrifugation (400 g for 5 min) the cells were suspended in 25 ml 20% FCS-DMEN (equilibrated) by gentle pipetting with the 24 ml pipette used for addition. The fusion mixture in 20% FCS-DMEN was then distributed in 0.5 ml aliquots into 48 Linbro wells containing 1.5 ml of equilibrated 20% FCS-DMEN.

As feeder cells, the remaining spleen cells were diluted and added dropwise at about $4 \times 10^5$/well. Culture trays were then incubated at 37° C. in an atmosphere of 5% $CO_2$ in air and over 45% humidity.

The following day (day 1) and on days 2, 3, 7 and 11 post cell fusion, the top half of each culture medium was removed (using a separate Pasteur pipette for each well to avoid possible cross contamination) and replaced with an equal volume of HAT selective medium (Littlefield, 1964) equilibrated with 5% $CO_2$ in air.

Cultures were inspected daily for hybrid growth and possible contamination with yeasts or microorganisms, leaving cultures outside the incubator as briefly as possible. When the growth of cell monolayer neared confluence (about 14–21 days after cell fusion)—about the same time that the medium was turning from (phenol) red to yellow—culture supernatants were first tested (by agglutination with A, B and O red cells). Positive cultures were subdivided that day by suspending the cells with a 1 ml pipette and transferring 1 ml of cell suspension to 1 ml of HAT medium (equilibrated, at 37° C.); the original culture was replenished with HAT medium. Split cultures were grown in separate incubators to guard against incubator failure and were periodically assayed by agglutination and frozen as early as possible in liquid $N_2$ in FCS containing 10% DMSO. Negative cultures were retested when the medium was yellow. Any contamination by yeasts or microorganisms was dealt with by adding 45% EtOH and after 5 min aspirating the culture and washing the empty well with EtOH. Any split medium on the culture tray was always immediately aspirated.

At 4–10 days after initial testing of fusion wells, subcultures were retested and aliquots of positive cultures were frozen or prepared for cloning.

Isolation of hybrid clones secreting anti-B

Cloning of cells from selected cultures was performed on soft agar, as described by Cotton et al (see above for reference). A solution of 0.5% agar in HAT medium was prepared by adding 50 ml of 1% agar (Difco Bacto) in 0.9% saline to 50 ml HAT-DMEN 2X (100 ml 2X DMEN+4 ml P/S+4 ml glut.+3 ml pyr.+75 ml FCS+7.8 ml 50X HAT), both at 45° C. The agar mixture was pipetted into 9 cm petri dishes (Nunc) at 15 ml/dish and allowed to set with the lid off inside a laminar flow tissue culture hood for 5 min, and then equilibrated in a gassed incubator for 30 min.

To 1 ml of cells in a series of 6 threefold dilutions in Linbro wells made DMEN, 1 ml 0.5% agar HAT-DMEN was added. The 2 ml mixture was evenly layered over the set agar, air dried as before and incubated at 37° C. in an atmosphere of 5% $CO_2$ in air.

After 14–20 days discrete macroscopic cell colonies had formed, many arising from single cells. These were picked from dishes containing the least number of colonies (normally 10–20) using a finely drawn Pasteur pipette, and seeded into Linbro wells containing 1 ml of HAT-DMEN equilibrated in a gassed incubator.

Following the usual cycle of culture growth, testing for agglutination, splitting up cultures and freezing some in liquid $N_2$, selected clones were weaned off HAT by serial transfer of half the culture to an equal volume of HT-medium for 2–3 passages and then to 20% FCS-DMEN, taking 5–6 days in all.

Cells were recloned as before but in 20% FCS-DMEN containing 0.5% agar. Twice cloned lines were selected (1) for the ability of culture supernatant to give strong agglutination with red cells and (2) for rapid high density cell growth. Chosen clones were adapted to growth in low FCS by serial transfer every 2 days of half the culture to media containing 10%, 5% and 2.5% FCS respectively.

Cloning by limiting dilution, with feeder cells

This method was used for hybrid cells which did not grow successfully when plated at low density on agar. Cell suspensions were diluted in a twofold series to 1 in 32 in Linbro wells, preparing several rows. To respective rows was added 100 µl of growth medium containing one of each of the following as feeder cells:

(1) $4 \times 10^5$ B10.BR thymus cells
(2) $4 \times 10^5$ B10.BR spleen cells
(3) $4 \times 10^5$ X irradiated 3T3 mouse fibroblast cells (20,000 rads at 1 rad/sec)
(4) $4 \times 10^5$ mitomycin treated* B10.BR thymus cells
(5) $4 \times 10^5$ nitomycin treated* B10.BR spleen cells
(6) Nil

*0.1 ml Mitomycin C (Sigma) at 0.5 mg/ml in EBSS was added to 1 ml of medium containing $10^7$ cells, followed by incubation for 30 min at 37° C. and 3 washes.

Hybrid cell growth was compared at low dilutions for suitability of picking isolated colonies.

Storage of hybrid cells in liquid $N_2$

Frozen hybrid stocks were prepared from exponentially growing cells at $2-8 \times 10^5$ cells/ml. Pelleted cells from 10 ml culture supernatant were resuspended in 2 ml of 90% FCS-10% DMSO (i.e. at about $10^6$/ml) and split into 2 sterile freezer vials ($10^6$/vials). Vials were cooled on ice for 2–4 h, then overnight in the vapour phase of a Linde liquid $N_2$ tank and finally immersed in liquid $N_2$. This should cool cells at about 1° C./min.

To grow cells from frozen stocks, a vial was rapidly thawed in a 37° C. water bath and the contents slowly diluted in 10 ml growth medium. Pelleted cells (400 g, 5 min) were resuspended in 5 ml 5–10% FCS-DMEN.

Vials of $10^7$ cells were prepared from spinner cultures so that a 50 ml culture could be immediately started.

Nomenclature of antibody secreting hybrid cells e.g. the anti-B producing clone NB1/19.112.28

Each hybrid is designated by a title which refers to the fusion experiment—in this case the N in NB1 refers to the parental myeloma NS1; B refers to anti-B spleen cells.

The first number—here 19—refers to the initial uncloned culture well from which that clone was derived.

Subsequent numbers—112 and 28—define the culture wells in which selected clones are grown following the first and second agar clonings respectively.

Culture wells in a Linbro tray are numbered 1–24 or lettered A1–1D6. Thus, if 5 trays are used, wells go from 1–120 or 1A1–5D6.

The complete designation refers to the cell clone, the produced monoclonal antibody and its antigenic specificity.

Characterisation of the Monoclonal Anti-B

Three stable tissue culture lines (NB1/19.112.28, NB1 6.36.36 and NB1/48.30.40) of cloned anti-B producing cell hybrids were derived from a fusion between mouse spleen cells primed by group B antigen and a mouse myeloma line. The tissue culture supernatant containing secreted monoclononal antibody was tested from each of the three lines separately.

Samples of human anti-B from the Blood Group Reference Laboratory (BGRL No. 7327) and from a commercial supplier were used, each taken from the same batch, to assess the efficiency of the monoclonal anti-B produced by the hybridoma cell.

Haemagglutination tests were carried out according to Dunsford and Bowley (see above). Red cells were from ACD or clotted samples (from the Regional Blood Transfusion Centre, Cambridge) less than 7 days old and were washed 4 times before use. 20% red cell suspensions in saline were used for tile tests and 2% suspensions for the standard 2 hour tube gravity sedimentation test. Enhancement tests used 2% papainized cell suspensions or 20% bovine albumin. Antibody dilutions were made in saline.

In the standard 2 hour tube sedimentation test, fully grown culture supernatants gave anti-B agglutination titres as shown in Table 1.

TABLE 1

| | Saline agglutination titres (+) of three monoclonal anti-B reagents compared with human anti-B | | | | |
|---|---|---|---|---|---|
| | Monoclonal anti-B | | | Human anti-B | |
| | NB 1/19.112.28 | NB 1/6.36.36 | NB 1/48.30.40 | BGRL 7327 | Commercial Serum |
| $A_1B$ | 1,024 | 32 | 16 | 32 | 256 |
| $A_2B$ | 2,048 | 64 | 256 | 32 | 512 |
| B | 2,048 | 64 | 512 | 32 | 512 |
| B cord* | 1,024 (512–1,024) | 16 (8–64) | 8 (4–8) | 16 (4–32) | NT |
| $A_1$ | 0 | 0 | 0 | 0 | 0 |
| 0 | 0 | 0 | 0 | 0 | 0 |

(+) Macroscopic end point.
*Average titres with 6 different blood samples (range in parenthesis).
NT Not tested.

The differences among the three monoclonal antibodies were repeatable in these and the other tests described. The antibody NB1/19.112.28 consistently gave excellent results.

As may be expected $A_1B$ adult and B cord cells gave slightly lower titres than adult $A_2B$ and B cells, reflecting the weaker B status of the former cell types.

All the reagents tested gave adequate agglutination with all cell types in the panel, but the activity of NB1/19.112.28 even with the 6 examples of weak cord bloods shown in the table was outstanding. The range of NB1/19.112.28 activity with five different A₁B bloods (not shown in the table) was 256–1024 (average titre 512), compared with 16.32 (average 32) using the BGRL anti-B. In a further experiment the saline agglutination titres of NB1/48 and NB1/19 purification products were measured with 2% B and A₁B cells. Fractions of purified NB1/48 and NB1/19 were microfuged and carefully diluted in PBS (phosphate buffered saline) until $A_{280}=1.00$ (i.e. at 100 μg/ml), assuming that $$A^{1\%}_{1\,cm,\,280} = 10.$$

Ammonium sulphate cuts of culture supernatant (from which the fractions were purified) were microfuged and diluted to 1/16 in P.B.S. Serial 2 fold dilutions were made in P.B.S. pH 7.4 by accurate pipetting with a Hamilton syringe rinsed four times between each pipetting section. 25 μl aliquots of each dilution were incubated in glass tubes with 25 μl of 2% red cells ($5\times10^6$) suspended in P.B.S. at pH 7.4 for 2 hours at room temperature. Cell pellets were carefully transferred onto glass slides and scored for agglutination. In this experiment culture supernatants used were as in Table 1 above. The results are given in Table 2

In tile agglutination tests which reflect antibody avidity, the weaker reactions of B cord and $A_1B$ adult cells, compared with adult B and $A_2B$ cells, discriminated more clearly the anti-B activities of the different reagents. These results are given in Table 3.

TABLE 3

| | Avidity times (secs) of monoclonal anti-B reagents compared with human anti-B | | | | |
|---|---|---|---|---|---|
| | Monoclonal anti-B | | | Human anti-B | |
| | NB 1/19.112.28 | NB 1/6.36.36 | NB 1/48.30.40 | BGRL 7327 | Commercial Serum |
| $A_1B$* | 5 (4–7) | 17 (10–25) | 21 (12–30) | 21 (15–32) | 4 (3–6) |
| $A_2B$ | 4 | 7 | 8 | 8 | 4 |
| B | 4 | 8 | 8 | 8 | 4 |
| B cord+ | 7 (6–9) | 22 (15–38) | 32 (16–47) | 22 (16–32) | 5 (4–5) |
| $A_1$ | — | — | — | — | — |
| O | — | — | — | — | — |

*Average of results with 20 different samples (range of times in parenthesis).
+Average of results with 8 different samples.

With A₁B and B cord cells monoclonal anti-B NB1/19.112.18, used unconcentrated and without additives, produced within seconds a strong agglutination reaction similar to that seen with the commercial reagent. Although the BGRL reagent gave macroscopically adequate results the speed and extent of clumping were inferior.

In a further experiment the tile agglutination times of 20% B and A₁B red cells by NB1/48 and NB1/19 purification products were measured. The reagents used were those described in relation to Table 2 except that the red cells were used at 20% 2 μl aliquots of each dilution were mixed with 20 μl of red cells on an opaque glass tile and rocked regularly. A pedal operated stop watch was started at the moment of mixing. Table 4 shows the time (sec) for agglutination to occur and the extent of agglutination after 5 minutes. The extent of agglutination is as defined in relation to Table 3, e.g. 13V indicates that+agglutination occured after 13 seconds and that there was very strong agglutination after 5 minutes.

TABLE 2

| | | Saline Agglutination Titres of NB 1/19 and NB 1/48 Purification Products | | | | | | | | | | | | |
|---|---|---|---|---|---|---|---|---|---|---|---|---|---|---|
| | | Reciprocal antibody dilution | | | | | | | | | | | | |
| | | N | 2 | 4 | 8 | 16 | 32 | 64 | 128 | 256 | 512 | 1024 | 2048 | (+) Titre |
| | NB 1/48 | | | | | | | | | | | | | |
| B | Culture supernatant | C | C | V | ++ | + | + | (+) | GW | W | W | — | — | 64 |
| | 70 × Amm. sulph. cut (1/16) | C | V | ++ | + | + | (+) | GW | GW | W | — | — | — | 32 |
| | Fraction 1 (100 μg/ml) | V | ++ | + | + | + | (+) | GW | W | W | — | — | — | 32 |
| $A_1B$ | Culture supernatant | + | + | (+) | (+) | (+) | W | — | — | — | — | — | — | 16 |
| | 70 × Amm. sulph. cut (1/16) | + | + | (+) | (+) | W | W | — | — | — | — | — | — | 8 |
| | Fraction 1 (100 μg/ml) | + | + | (+) | GW | W | — | — | — | — | — | — | — | 4 |
| | NB 1/19 | | | | | | | | | | | | | |
| | Culture supernatant | C | C | C | C | V | V | ++ | + | + | (+) | — | — | 512 |
| | 125 × Amm. sulph. cut (1/16) | C | C | C | V | V | V | ++ | + | (+) | (+) | — | — | 512 |
| | Fraction 2 (100 μg/ml) | V | V | V | ++ | + | + | (+) | — | — | — | — | — | 64 |
| $A_1B$ | Culture supernatant | C | C | V | V | V | ++ | ++ | + | (+) | GW | W | W | 256 |
| | 125 × Amm. sulph. cut (1/16) | C | V | V | ++ | ++ | ++ | + | + | (+) | (+) | W | W | 512 |
| | Fraction 2 (100 μg/ml) | V | ++ | ++ | ++ | + | + | + | GW | GW | W | — | — | 64 |

In Table 2:
C means "complete agglutination"
V means "very strong agglutination"
++
+ intermediate degrees of agglutination
(+)
GW means "getting weak"
W means "weak"

TABLE 4

Tile Agglutination (sec) of 20% B and A₁B red cells by NB 1/19 and NB 1/48 Purification Products

| | | Reciprocal antibody dilution | | | | |
|---|---|---|---|---|---|---|
| | | N | 2 | 4 | 8 | 16 |
| NB 1/48 | | | | | | |
| B | Culture supernatant | 11 v | 16 v | 28++ | 52+ | NT |
| | 70 × Amm. sulph. cut (1/16) | NT | 18++ | 32+ | NT | NT |
| | Fraction 1 (100 µg/ml) | 12++ | 21+ | 41+ | NT | NT |
| A₁B | Culture supernatant | 78+ | 101+ | NT | NT | NT |
| | 70 × Amm. sulph. cut (1/16) | NT | 209+ | NT | NT | NT |
| | Fraction 1 (100 µg/ml) | 79+ | >180+ | NT | NT | NT |
| NB 1/19 | | | | | | |
| B | Culture supernatant | 3 c | 5 c | 7 v | 10 v | NT |
| | 125 × Amm. sulph. cut (1/16) | NT | 5 c | 8 v | 10 v | 19++ |
| | Fraction 2 (100 µg/ml) | 6 v | 10 v | 25++ | NT | NT |
| A₁B | Culture supernatant | 9 v | 13 v | 20 v | 31++ | NT |
| | 125 × Amm. sulph. cut (1/16) | NT | 11 v | 17 v | 19++ | NT |
| | Fraction 2 (100 µg/ml) | 23 v | 33 v | 71++ | NT | NT |

The results obtained with doubling dilutions of different reagents are given in Table 5 and are an indication of the relative potency of NB1/19.112.28. Diluted fourfold, for example, the preparation of culture supernatant under test gave a satisfactory reaction with A₁B cells relative to the commercially available anti-B serum.

TABLE 5

Effect of dilution on avidity times (secs) of anti-B reagents with A₁B cells

| | Dilution factor | | | | |
|---|---|---|---|---|---|
| | 1 | 2 | 4 | 8 | 16 |
| NB 1/19.112.28* | 5 | 7 | 10 | 16 | 26 |
| BGRL anti-B serum | 19 | >100 | — | — | — |
| Commercial anti-B serum | 4 | 6 | 12 | 22 | 57 |

*Gives a titre of 1:512 with A₁B cells used in this test.

Not every monoclonal antibody with ABO specificity is equally suitable for blood grouping. In the examples given here two of the three monoclonal anti-B were less adequate blood grouping reagents, although their properties were comparable to the BGRL standard.

The specificity of the monoclonal anti-B allows for a quantitative functional affinity to be measured. The functional affinity may be expressed in two ways.

Figure 1:
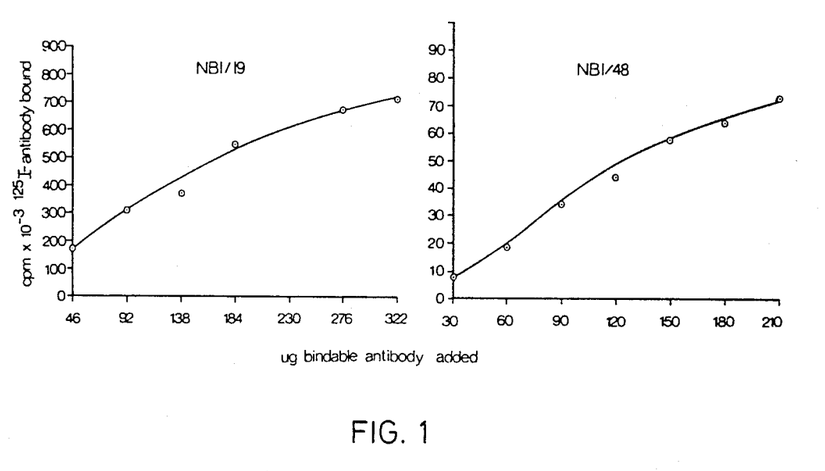
FIG. 1 is a graph of the equilibrium binding of $^{125}I$-labelled anti-B antibodies with group B erythrocytes.

Firstly the functional affinity may be expressed as an equilibrium constant for the association reaction between a molecule of monoclonal anti-B IgM and a B determinant (of the corresponding immunochemical type) upon an erythrocyte. The equilibrium constant (hereafter K) is obtained by first measuring the equilibrium binding amount of $^{125}$I-labelled anti-B antibodies with group B erythrocytes at different levels of bindable antibody present in solution. The experiment was performed as follows:

All assays were performed in duplicate. Linear dilution series of $^{125}$I-labelled NB1/19 and NB1/48 were prepared in buffer (0.8% BSA-EBSS+10 mM Hepes+0.1% NaN₃ pH 7.4) by accurate pipetting using a Hamilton syringe rinsed 5 times between tubes. 25 µl portions of $^{125}$I-labelled antibody were added to 1.5 ml Beckman microfuge tubes followed by 15 µl of buffer containing 2×10⁶ fresh group B cells. Assay mixtures were incubated at 4° C. on a roller. At 6 h 1.5 ml of ice cooled buffer was rapidly added, and immediately followed by a 15 sec. microfuge spin and removal of the supernatant, the time form addition of buffer to switching on the microfuge being 2-4 sec. In control incubations, 2×10⁶ A₁ cells replaced B cells, and the binding of $^{125}$I-labelled NB1/19 and NB1/48 which was respectively 1.2-2.0% and 0.9-1.2% of added bindable counts was subtracted from the experimental values. The results are shown in FIG. 1 in which the amount of $^{125}$I-antibody bound (cpm×10$^{-3}$) is plotted against the amount of bindable antibody added (µg) for NB1/19 and NB1/48. It is possible from these graphs to prepare a modified Scratchard plot of the equilibrium binding characteristics of $^{125}$I-labelled anti-B with group B erythrocytes. Such a graph is given in FIG. 2, in which values are shown for both NB1/19 and NB1/48, the latter being presented on a larger scale in the inset graph. In both cases extropolation to the x-axis gives the amount of antibody bound at saturation.

Figure 2:
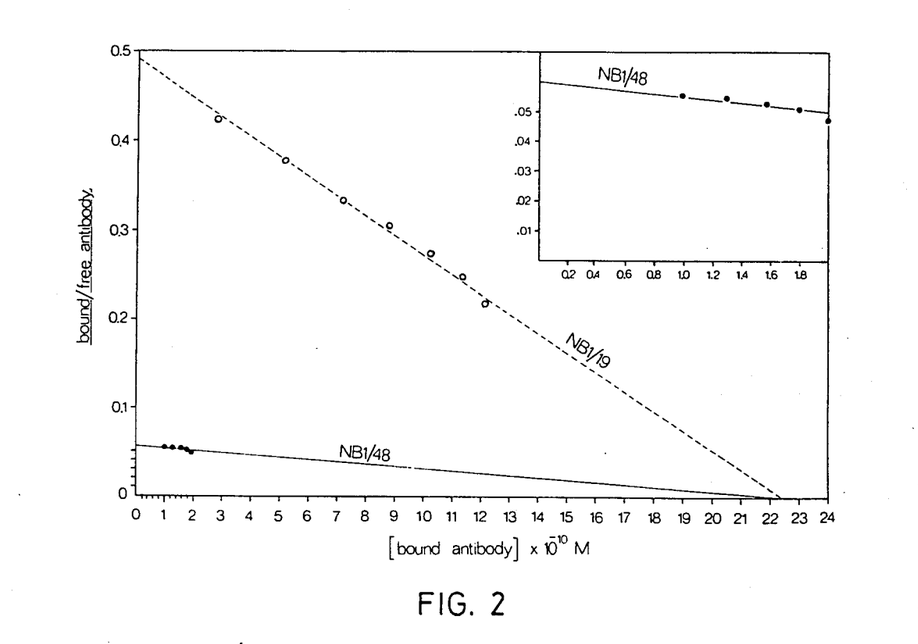
FIG. 2 is a modified Scratchard plot of the equilibrium binding of $^{125}I$-labelled anti-B antibodies with group B erythrocytes.

The equilibrium constant may be readily calculated from the Scratchard plot.

In the alternative the functional affinity may be expressed as a dissociation rate constant for the dissociation reaction of an immunocomplex formed between a molecule of monoclonal anti-B IgM and a B-determinant (of the corresponding immunochemical type) upon an erthyrocyte. The dissociation rate constant (hereafter $K_{-1}$) may be calculated from a graph of the dissociation with time of $^{125}$I-labelled monoclonal anti-B from erythrocytes by measuring the gradient of a tangent to the dissociation curve constructed through zero time.

Figure 3:
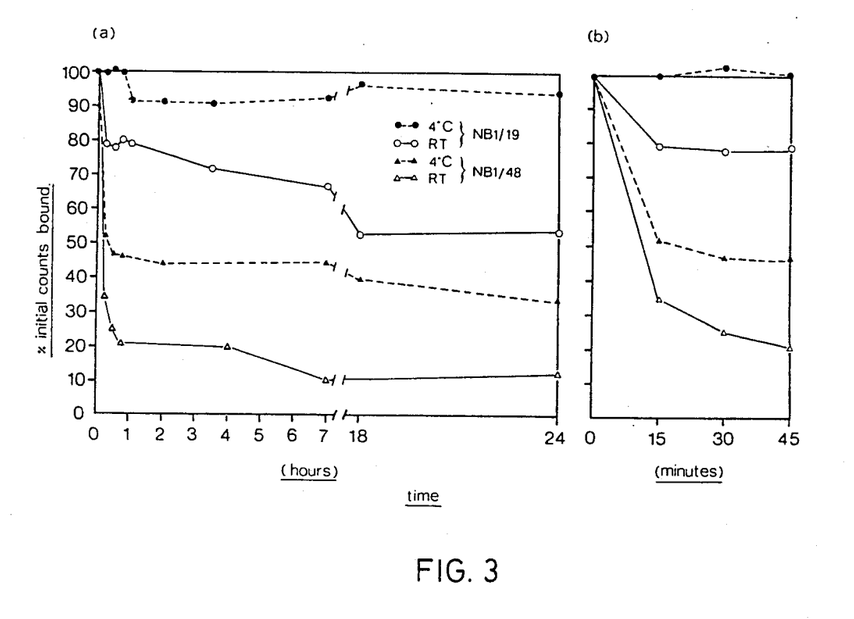
FIG. 3 is a graph showing the dissociation rate of $^{125}I$-labelled anti-B antibodies from group B erythrocytes at 4° C. and at room temperature.

In one experiment the rate of dissociation of $^{125}$I-labelled anti-B antibody from group B erythrocytes at 4° C. and RT was measured, in conditions of cold antibody excess. 25 µl portions of $^{125}$I-labelled NB1/19 (bindable antibody: 6.0×10⁵ cpm, 50 ng) or NB1/48 (9.0×10⁵ cpm; 124 ng) were added to 1.5 ml microfuge tubes, followed by 25 µl of buffer (0.8% BSA-EBSS+10 mM Hepes+0.1% NaN₃ pH 7.4) containing 2×10⁶ group B erythrocytes. The mixtures were incubated at 4° C. on a roller. After 1 h, to 4 of these tubes 1.5 ml of ice cool buffer was rapidly added and the cells were immediately pelleted with a 15 sec. spin in an Eppendorf microfuge. The supernatant was rapidly removed and the cells transferred for measurement of bound radioactivity (cpm).

To the remaining assay tubes incubated 2 h was added 25 µl of a 125 times ammonium sulphate concentrate of NB1/19 culture supernatant, diluted 1/10 in buffer. The 75 µl mixtures were then incubated at 4° C. or RT on a roller. At various time (15 min-24 h) 1.5 ml of cold buffer was added, and the cells were immediately pelleted and counted as above. In control incubations 2×10⁶ Al cells replaced group B cells, and the binding of NB1/19 and NB1/48 after an incubation of 1 h at 4° C. which was 1.1% and 1.9% of the added counts were substracted from the experimental values. Binding was then expressed as a percentage of the counts bound at the end of the 2 h preincubation period. 100% binding by $^{125}$I-labelled NB1/19 and NB1/48 was $9.1 \times 10^4$ cpm and $715 \times 10^4$ cpm respectively.

In the final reaction mixture, cold NB1/19 was present in at least 40 fold excess over labelled antibody, assuming that the concentration of monoclonal antibody in culture supernatant is at least 10 μl/ml.

The results are shown in FIG. 3 in which:
(a) shows dissociation over a 24 hr period, and
(b) shows the first 45 min replotted on an expanded time scale.

Figure 4:
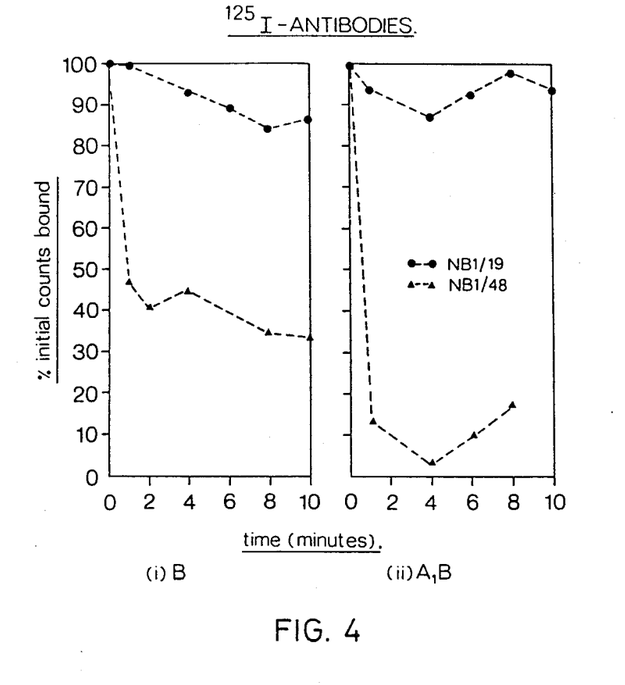
FIG. 4 is a graph showing the dissociation rate of $^{125}$I-labelled anti-B antibodies from $2 \times 10^6$ or $A_1B$ erythrocytes at room temperature.

In a further experiment the rate of dissociation of $^{125}$I-labelled anti-B antibodies from $2 \times 10^6$ B or A$_1$B erythrocytes at RT. in conditions of cold antibody excess. Experimental procedures were identical to those described in FIG. 6.19, except that following the addition of cold antibody to antigen-labelled antibody complex, the cells were pelleted at 2 min intervals throughout at 10 min period. Treatment of results were identical. The following values were used or obtained:

|  |  | Added bindable $^{125}$I-ab | | Background × A$_1$ cells (1% added | 100% binding values |
|---|---|---|---|---|---|
|  |  | (cpm) | (ng) | cpm) | (cpm) |
| FIG. (i) | [NB 1/19: | $6.9 \times 10^5$ | 58 | 0.3% | $1.3 \times 10^5$ |
|  | [NB 1/48: | $9.0 \times 10^5$ | 124 | 0.5% | $5.2 \times 10^4$ |
| FIG. (ii) | [NB /1/19: | as above | | as above | $3.7 \times 10^4$ |
|  | [NB 1/48: |  |  |  | $4.1 \times 10^3$ |

The results are shown in FIG. 4 in which:
graph (i) represent B group erythrocytes and
graph (ii) represents A$_1$B group erythrocytes.

The functional affinities measured by the above experiments and the characteristics measured by other tests described above are summarised below in respect of NB1/19.112.18 and NB1/48.30.40.

TABLE 6

Characteristics of the monoclonal anti-B antibody NB 1/19.112.28 on B and A$_1$B red cells

|  | K$^a$ (M$^{-1}$) | k$^b$ (sec$^{-1}$) | Agglutination$^c$ time (sec) at 100 μg/ml IgM | Titre$^d$ at 100 μg/ml IgM | μg IgM$^e$ req. for $4 \times 10^6$ red cells |
|---|---|---|---|---|---|
| B | $2.3 \times 10^8$ | $3.8 \times 10^{-4}$ | $6 \pm 2$ | 64 (32–64) | 0.31 |
| A$_1$B | NT | $.17 \times 10^{-3}$ | $23 \pm 5$ | 64 (32–64) | 1.20 |

$^a$ = Scatchard derived equilibrium constant
$^b$ = dissociation constant for $^{125}$I antibody (10 minute curve)
$^c$ = tile agglutination × 20% cells in saline: 25 μl antibody + 25 μl cells
$^d$ = 2 h tube agglutination × 20% cells in saline: 25 μl antibody + 25 μl cells
$^e$ = the amount of antibody required to just produce complete agglutination of $4 \times 10^6$ red cells in a reaction volume of 50 μl ie in a 2 h tube agglutination × 2% cells in saline using 25 μl antibody at various concentrations + 25 μl red cells.
NT = not tested

TABLE 7

Characteristics of the monoclonal anti-B antibody NB 1/48.30.40 on B and A$_1$B red cells

|  | K (M$^{-1}$) | k$_{-1}$ (sec$^{-1}$) | Agglutination time (sec) at 100 μg/ml IgM | Titre at 100 μg/ml IgM | μg IgM req. for $4 \times 10$ red cells |
|---|---|---|---|---|---|
| B | $2.7 \times 10^7$ | $1.1 \times 10^{-2}$ | $12 \pm 4$ | 32 (16–32) | 5.0 |
| A$_1$B | NT | $2.5 \times 10^{-2}$ | $79 \pm 20$ | 4 (2–8) | 20.0 |

Finally some experiments were conducted to assess the efficacy of NB1/19.112.28 as a blood grouping reagent in automatic grouping machines, its selectivity when using papainized red blood cells, and its thermal stability.

Automated blood typing tests were performed with the latest Autogrouper 16C with optical density reading and microprocessor printout. The reagents were enhanced using 1% methyl cellulose and 0.25% bromelin.

Monoclonal antibody NB1/19.112.28 culture supernatant diluted 1 in 15 was assessed on the autogrouper 16C with 844 citrated donor bloods. The results shown in Table 8 were excellent and were the same as those obtained using BGRL anti-B diluted 1 in 10 on the same samples. Neither reagent gave false positive or false negative results.

TABLE 8

Automated donor grouping with monoclonal anti-B NB 1/19.112.28

|  | Number tested | Positive reactions | Negative reactions |
|---|---|---|---|
| A$_1$B | 28 | 28 | 0 |
| A$_2$B | 5 | 5 | 0 |
| B | 64 | 64 | 0 |
| A | 355 | 0 | 355 |
| O | 392 | 0 | 392 |

In the tube and tile saline tests described above, and in the automated tests using cells enhanced with 1% methyl cellulose and 0.25% bromelin, monoclonal anti-B never reacted with A$_1$ or O cells. The anti-B specificity of NB1/19.112.28 was also maintained with papainized red cells and using 20% albumen as shown in Table 9 below. Marginal enhancement of NB1/19.112.28 agglutination activity was seen in these tests and was most noticeable with papainized A$_1$B cells.

TABLE 9

Effect of papain and 20% albumin on agglutination titres at room temperature

|  | Monoclonal anti-B NB 1/19.112.28 | | | Human anti-B BGRL 7327 | | |
|---|---|---|---|---|---|---|
|  | Saline | Papain | Albumin | Saline | Papain | Albumin |
| A$_1$B | 256 | 1,024 | 512 | 16 | 32 | 16 |
| A$_2$B | 512 | 1,024 | 1,024 | 32 | 32 | 64 |
| B | 512 | 1,024 | 1,024 | 32 | 64 | 32 |
| A$_1$ | — | — | — | — | — | — |
| O | — | — | — | — | — | — |

In tests for stability 2 ml aliquots of undiluted NB1/19.112.28 culture supernatant were exposed to different conditions and retested at room temperature for titre and avidity.

Repeated freezing and thawing (see Table 10) failed to reduce the level of anti-B activity.

TABLE 10

Stability of monoclonal anti-B
(NB 1/19.112.28) to freeze/thawing.

| No. of freeze/thawings | Agglutination titre × $A_1B$ cells | Avidity time (sec) × $A_1B$ cells | |
|---|---|---|---|
| | | 1:1 sup | *1:2 sup |
| × 1 | 1,024 | 5 | 7 |
| × 2 | 1,024 | 4 | 7 |
| × 3 | 1,024 | 5 | 7 |
| × 4 | 1,024 | 5 | 7 |
| × 5 | 512 | 5 | 7 |

*Dilutions made following treatment of neat supernatant (Sup.)

Tests of thermal stability over short periods (see table 11) indicate that monoclonal anti-B is stable to storage at −20° C. and 4° C., and to incubation at 56° C.

TABLE 11

Temperature sensitivity of NB 1/19.112.28

| Treatment | Saline titre × $A_1B$ cells | Avidity time (sec) × $A_1B$ cells | | |
|---|---|---|---|---|
| | | 1:1 sup | *1:2 sup | *1:4 sup |
| 2 wks at −20° C. | 512 | 5 | 7 | 10 |
| 1 wk at 4° C. | 512 | 5 | 6 | 9 |
| 24 h at 20° C. | 512 | 5 | 7 | 9 |
| 24 h at 37° C. | 512 | 5 | 6 | 9 |
| ½ h at 56° C. | 512 | 5 | 6 | 9 |

*Dilutions made after treatment of neat supernatant (Sup.)

Neat culture supernatant has a potency at least equal to that of a hyperimmune commercial reagent, without the use of additives. It gives a rapid tightly agglutinated tile reaction suitable for detecting the weaker types of B ($A_1B$ and B cord cells) encountered in routine grouping work. It can also be used reliably for automated typing.

Twice cloned antibody-producing hybrid cell lines have been adapted to growth in large tissue culture vessels and, on repeated passage, continue to secrete antibody of uniform properties. Large volumes of active culture supernatant generated by continuous growth have the advantage of requiring far fewer screening tests than is currently needed to produce the same volume of human reagent from a large number of individually-screened serum donations, considerably easing the testing workload. Moreover, the low cost of £5 for the materials to make 1 liter of potent culture supernatant could be further reduced by using an acceptably diluted (Table 5) preparation of active supernatant.

We claim:

1. A monoclonal antibody which has specificity for an antigenic determinant of a B-type blood cell wherein the monoclonal antibody is produced from a hybridoma cell-line produced by the fusion of a myeloma cell with a lymphocyte derived from a mouse inoculated with B-type blood antigen.

2. A monoclonal antibody of claim 1 capable of causing agglutination of sample of B-type blood cells having the said determinant.

3. A monoclonal antibody as claimed in claim 1 which is such that the equilibrium constant of the interaction between said antibody and B-type blood cells is greater than $1.3 \times 10^7 \, M^{-1}$.

4. A monoclonal antibody as claimed in claim 3 which is such that the equilibrium constant of the interaction between said antibody and B-type blood cells is greater than $1.2 \times 10^8 \, M^{-1}$.

5. A monoclonal antibody as claimed in claim 2 which is such that the equilibrium constant of the interaction between said antibody and B-type blood cells is greater than $1.3 \times 10^7 \, M^{-1}$.

6. Hybridoma cells capable of secreting monoclonal antibodies as claimed in claim 2.

* * * * *